(12) United States Patent
Bogue

(10) Patent No.: US 8,113,235 B2
(45) Date of Patent: Feb. 14, 2012

(54) APPARATUS AND METHODS FOR FACILITATING PROSTHESIS DONNING, DOFFING, RETENTION, AND FIT

(76) Inventor: David Robert Bogue, Layton, NJ (US)

( * ) Notice: Subject to any disclaimer, the term of this patent is extended or adjusted under 35 U.S.C. 154(b) by 803 days.

(21) Appl. No.: 12/245,006

(22) Filed: Oct. 3, 2008

(65) Prior Publication Data
US 2010/0087931 A1 Apr. 8, 2010

(51) Int. Cl.
*F16K 15/14* (2006.01)
(52) U.S. Cl. .............. 137/522; 251/82; 623/34
(58) Field of Classification Search .......... 137/522; 251/82; 623/34
See application file for complete search history.

(56) References Cited

U.S. PATENT DOCUMENTS

| | | | |
|---|---|---|---|
| 2,533,404 A | 12/1950 | Sharp et al. | |
| 2,569,790 A | 10/1951 | White et al. | |
| 3,505,687 A | 4/1970 | Prahl | |
| 2,790,180 A | 4/1975 | Hauser | |
| 5,201,774 A | 4/1993 | Greene | |
| 5,658,353 A | 8/1997 | Layton | |
| 5,771,924 A * | 6/1998 | Huygen | 137/522 |
| 6,334,876 B1 | 1/2002 | Perkins | |
| 6,544,292 B1 | 4/2003 | Laghi | |
| 6,979,355 B1 | 12/2005 | Slemker | |
| 2005/0131550 A1 | 6/2005 | Coop | |
| 2006/0079965 A1 | 4/2006 | Benson | |
| 2007/0055383 A1 | 3/2007 | King | |
| 2007/0112440 A1 | 5/2007 | Perkins et al. | |
| 2007/0265711 A1 | 11/2007 | Klein | |
| 2008/0086218 A1 | 4/2008 | Egilsson | |
| 2008/0147202 A1 | 6/2008 | Danzig et al. | |

FOREIGN PATENT DOCUMENTS

| | | |
|---|---|---|
| TW | 0298422 Y | 10/2006 |
| WO | WO 84/00881 A1 | 3/1984 |
| WO | WO 2008/061500 A2 | 5/2008 |

OTHER PUBLICATIONS

WWW.KINGSLEYMFG.COM, Advertisement for Quick Change Suction Valve printed on Aug. 18, 2008 from http://www.kingsleymfg.com/KMFGStore/Catalog_Product.asp?dept_id=0AFDB5C5-319 . . . , 1 page.

* cited by examiner

*Primary Examiner* — Kevin L Lee
*Assistant Examiner* — Macade Brown
(74) *Attorney, Agent, or Firm* — Chipperson Law Group

(57) ABSTRACT

Apparatus and methods for improved prosthesis donning, doffing, retention, and fit. A valve located in a prosthetic socket port includes a body, a core, a spring located partially within the core, a diaphragm, and a maintained operator. The operator includes a recess and a protrusion. The operator may be indexed to a displacement or vent position. When the operator is indexed to the displacement position, a tip of the core is pressed against the recess via the spring, and the diaphragm displaces any air that enters into the prosthetic socket when a load is applied to the residual limb. When the operator is laterally actuated, it is indexed to the vent position and the core tip moves from the recess to the protrusion. In this position, the diaphragm opens the socket cavity to the external atmosphere via valve vents, thereby facilitating prosthesis donning and doffing.

16 Claims, 5 Drawing Sheets

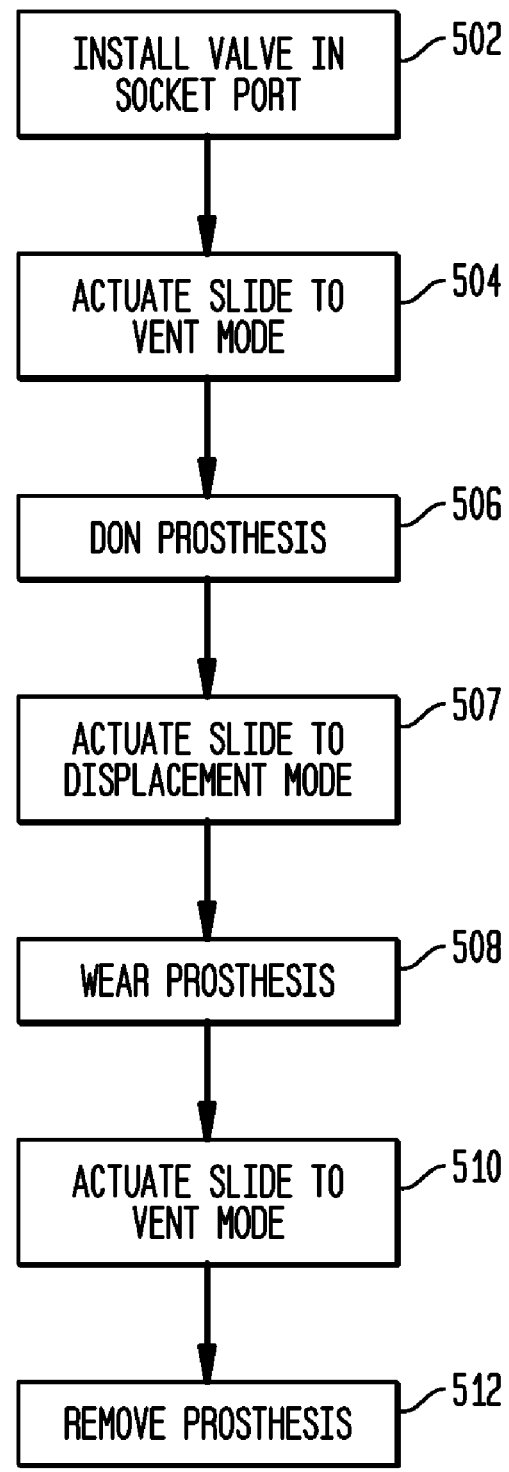

APPARATUS AND METHODS FOR FACILITATING PROSTHESIS DONNING, DOFFING, RETENTION, AND FIT

BACKGROUND OF THE INVENTION

Embodiments of the present invention generally relate to apparatus and methods for facilitating donning and doffing of a prosthesis and improving the retention and fit thereof. More specifically, the present invention relates to apparatus and methods for facilitating donning and doffing of a prosthesis and improving the retention and fit thereof via inclusion of a prosthetic valve having a slideable, maintained release mechanism.

Various prosthetic devices for limb replacement are known in the art. Many such prosthetic devices include a socket that serves as the connection between the user (i.e., the amputee) and the prosthesis. For load bearing prostheses (e.g., lower limb prostheses such as above the knee prostheses), the weight of the amputee is transferred to the ground via the socket.

For most users, a socket-type prosthesis is suspended by a negative pressure or vacuum created by the distal motion of the prosthetic socket relative to the residual limb. In order to don (i.e., put on) the prosthetic device, the user pulls the prosthesis over the residual limb until the residual limb is fully inserted into the socket. The socket is typically reduced to provide some compression on the limb. This compression creates a seal between the residual limb and the interior wall of the prosthetic socket such that any distal motion of the prosthetic socket relative to the residual limb will create a slight vacuum that retains the prosthesis (e.g., during the swing phase of walking). The successful fitting of a prosthetic socket results in the effective transfer of forces from the residual limb to the prosthetic socket such that the amputee can maintain daily activities without tissue damage or pain.

Socket-type prostheses known in the art typically include a port extending from the prosthetic socket to the environment external to the socket. During use of the prosthesis, some such ports are closed to the environment via a plug or a valve such that a vacuum is maintained within the prosthetic socket. Some such valves include adjustable or non-adjustable leak rates to bleed air introduced into the prosthetic socket. Other known valves include a pressure relief mechanism. These valves (e.g., one way check valves) are typically set to a predetermined setpoint (e.g., ½ PSI) to allow the valves to completely displace any air that enters into the prosthetic socket when a load is applied to the residual limb (e.g., when the user places pressure on the prosthesis during a step). This displacement ensures a comfortable and reliable fit of the prosthesis.

When a user wishes to remove a prosthesis, it is necessary to relieve the vacuum, or near vacuum, created within the prosthetic socket. In some known embodiments, this vacuum relief is accomplished via removal of the plug installed in the prosthetic socket port. This may be a cumbersome task as many such plugs must be unscrewed. In other known embodiments, this vacuum relief is accomplished via actuating the valve located in the prosthetic socket port to relieve the vacuum. A variety of actuation apparatus and methods are known. Some such valves require the user to maintain a button in a depressed position until the residual limb is fully removed from the socket. This type of removal may also be difficult for a user.

BRIEF SUMMARY OF THE INVENTION

Briefly stated, in one aspect of the present invention, an apparatus for facilitating prosthesis donning and doffing is provided. This apparatus includes: a body including a body cavity, at least one internal vent, and at least one external vent; a core, the core including a core tip, a core cavity, and a diaphragm interface, the core located at least partially within the body cavity; a core spring located at least partially internal to the core cavity, a first end of the core spring in contact with a surface of the core cavity, a second end of the core spring in contact with a surface of the body cavity; an operator, the operator including an operator aperture; an operator retainer, the operator retainer including a base and a head, an external surface of the head coupled to an interior surface of the operator aperture, the base including a recess and an operator retainer protrusion, the operator retainer protrusion located external to the periphery of the recess, an uppermost point of the recess in contact with the core tip when the operator is axially centered relative to the apparatus, an inwardly facing surface of the operator retainer protrusion in contact with the core tip when the operator is indexed to an off-center position, the operator maintained in an axially centered position due to the contact of the recess with the core tip, the operator maintained in an off-center position due to the contact of the inwardly facing surface of the operator retainer protrusion with the core tip; and a diaphragm, the diaphragm including a diaphragm aperture, the core passing through the diaphragm aperture, the diaphragm in contact with the diaphragm interface when the operator is axially centered relative to the apparatus, the diaphragm separated from the diaphragm interface when the operator is indexed to an off-center position.

In another aspect of the present invention, an apparatus for facilitating prosthesis donning and doffing is provided. This apparatus includes: a body including a centrally located body cavity, at least one internal vent, at least one external vent, a diaphragm bead body recess, and a cap body recess; a core, the core including a core tip, a core cavity, and a diaphragm interface, the core located at least partially within the body cavity; a core spring located at least partially internal to the core cavity, a first end of the core spring in contact with a surface of the core cavity, a second end of the core spring in contact with a surface of the body cavity; an operator, the operator including an operator aperture; an operator retainer, the operator retainer including a base and a head, an external surface of the head coupled to an interior surface of the operator aperture, the base including an operator retainer recess, and an operator retainer protrusion, the operator retainer protrusion located external to the periphery of the operator retainer recess, an uppermost point of the operator retainer recess in contact with the core tip when the operator is axially centered relative to the apparatus, an inwardly facing surface of the operator retainer protrusion in contact with the core tip when the operator is indexed to an off-center position, the operator maintained in an axially centered position due to the contact of the operator retainer recess with the core tip, the operator maintained in an off-center position due to the contact of the inwardly facing surface of the operator retainer protrusion with the core tip, the operator retainer including an operator retainer ledge, the operator retainer ledge located external to a cap recess when the operator is axially centered relative to the apparatus, the operator retainer ledge located internal to the cap recess when the operator is indexed to an off-center position; a diaphragm, the diaphragm including a diaphragm aperture, the core passing through the diaphragm aperture, the diaphragm in contact with the diaphragm interface when the operator is axially centered relative to the apparatus, the diaphragm separated from the diaphragm interface when the operator is indexed to an off-center position; a diaphragm backer, the diaphragm backer shaped as a disc having a diaphragm backer protrusion located on an upwardly facing surface of the disc; a diaphragm spring, a first end of the diaphragm spring encircling an outwardly facing surface of a bottommost portion of the operator retainer base, a second end of the diaphragm spring encircling an outwardly facing surface of the diaphragm backer protrusion; and a cap, the cap including a cap aperture, a cap recess, at least one cap vent, and a cap bead, the core passing at least partially into the cap aperture, the operator retainer passing at least partially into the cap aperture, the cap bead having a first external surface with a nearly identical shape as a first internal surface of the cap body recess for interlocking the cap with the body, the cap vent passing radially through a wall of the cap.

In yet another aspect of the present invention, a method of facilitating prosthesis donning and doffing is provided, wherein the prosthesis includes a socket and the socket includes a socket port. This method includes the following steps: installing a valve in the socket port, the valve including a two position maintained operator for indexing the valve to displacement mode or vent mode, the valve displacing air that enters into the socket of the prosthesis when a load is applied to the residual limb when the valve is indexed to the displacement mode, the valve opening the socket to an atmosphere external to the valve when the valve is indexed to the vent mode; actuating the maintained operator to the vent mode; donning the prosthesis; actuating the maintained operator to the displacement mode; wearing the prosthesis; actuating the maintained operator to the vent mode; and removing the prosthesis.

In a further aspect of the present invention, a method of facilitating prosthesis donning and doffing is provided, wherein the prosthesis includes a socket and the socket includes a socket port. This method includes the following steps: installing a valve in the socket port, the valve including a two position maintained operator for indexing the valve to displacement mode or vent mode, the valve displacing any air entering the socket when the valve is indexed to displacement mode, the valve opening the socket to an atmosphere external to the valve when the valve is indexed to the vent mode; actuating the maintained operator to the vent mode; donning the prosthesis; actuating the maintained operator to the displacement mode; wearing the prosthesis; actuating the maintained operator to the vent mode; and removing the prosthesis.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings:

FIG. 5 depicts a flowchart of the steps of a method for using a prosthetic valve in accordance with one embodiment of the present invention.

DETAILED DESCRIPTION OF THE INVENTION

Figure 1:
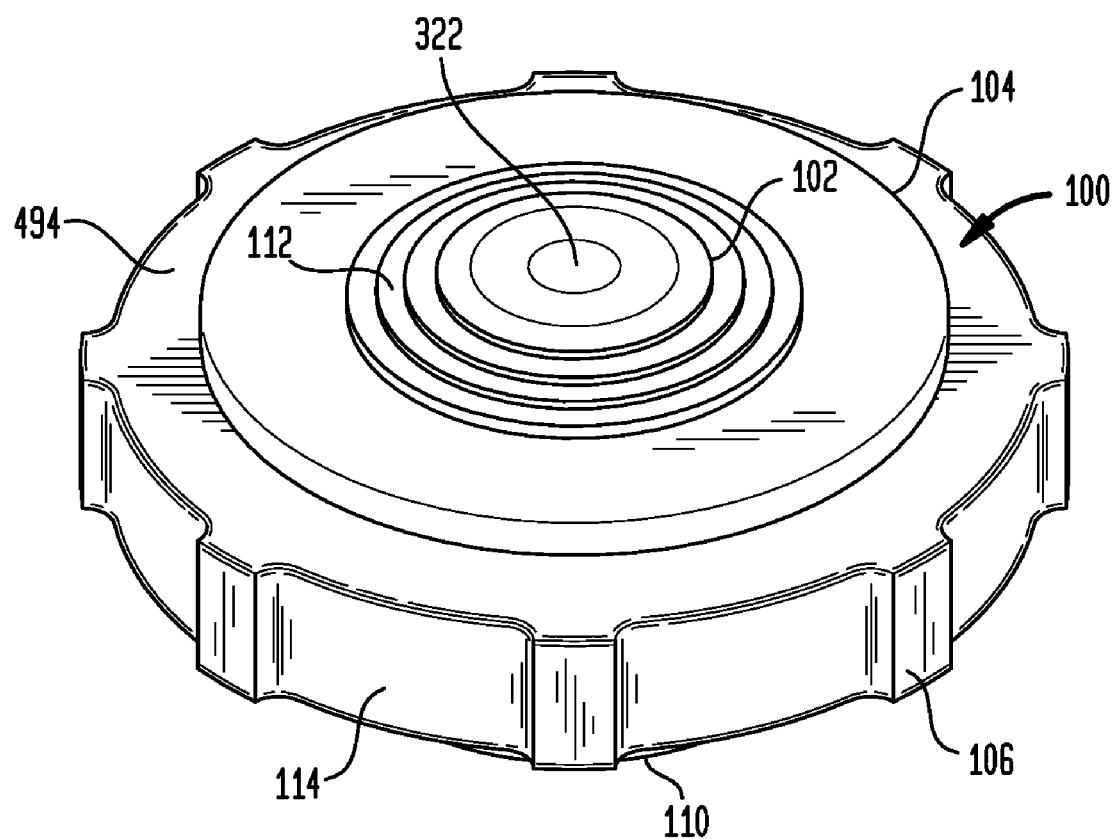
FIG. 1 is a perspective view of a prosthetic valve removed from its associated housing in accordance with one embodiment of the present invention.

Certain terminology may be used in the following description for convenience only and is not limiting. The words "lower" and "upper" and "top" and "bottom" designate directions in the drawings to which reference is made. The terminology includes the words above specifically mentioned, derivatives thereof and words of similar import.

Where a term is provided in the singular, the inventors also contemplate aspects of the invention described by the plural of that term. As used in this specification and in the appended claims, the singular forms "a", "an" and "the" include plural references unless the context clearly dictates otherwise, e.g., "a vent" includes a plurality of vents. Thus, for example, a reference to "a method" includes one or more methods, and/or steps of the type described herein and/or which will become apparent to those persons skilled in the art upon reading this disclosure.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods, constructs and materials are now described. All publications mentioned herein are incorporated herein by reference in their entirety. Where there are discrepancies in terms and definitions used in references that are incorporated by reference, the terms used in this application shall have the definitions given herein.

Referring first to FIG. 1, depicted is a perspective view of valve 100 in accordance with one embodiment of the present invention. Valve 100 includes, inter alia, operator 102, cap 104, body 106, and operator retainer 322. Valve 100 is designed for insertion into a socket port of a socket-type prosthesis. Valve 100 completely displaces any air that enters into the prosthetic socket. For example, air may enter the prosthetic socket while a user is sitting, during the swing phase of walking, due to manual release of the air by the user for comfort purposes, etc.). Such air may pass into the prosthetic socket via a plurality of paths. Most commonly, the air enters the socket via the proximal rim of the socket, however, air may also enter through the valve if, for example, the valve malfunctions due to the presence of debris or the valve is incorrectly installed. When using valve 100, any air present in the prosthetic socket is displaced as soon as a load is applied to the residual limb, for example, when the user stands and during the step phase of walking as described in greater detail below. Valve 100 is also designed to provide easy donning and doffing of the prosthesis and improved retention and fit via operator 102 as also discussed in greater detail below.

Figure 2:
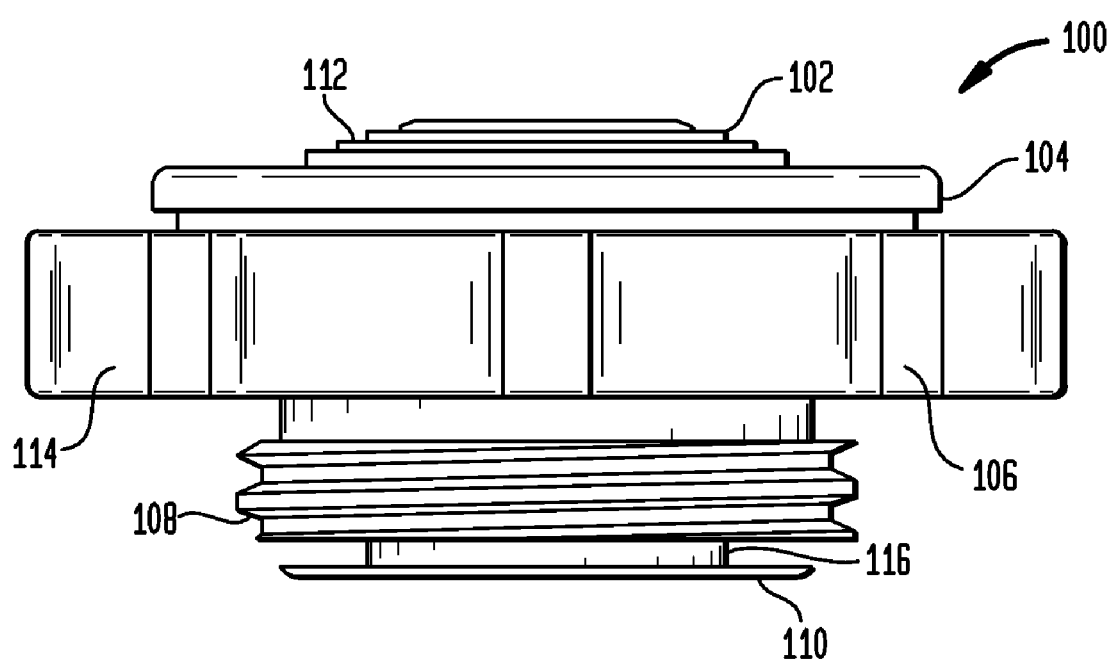
FIG. 2 is a side elevational view of the prosthetic valve of FIG. 1 removed from its associated housing.
Figure 3:
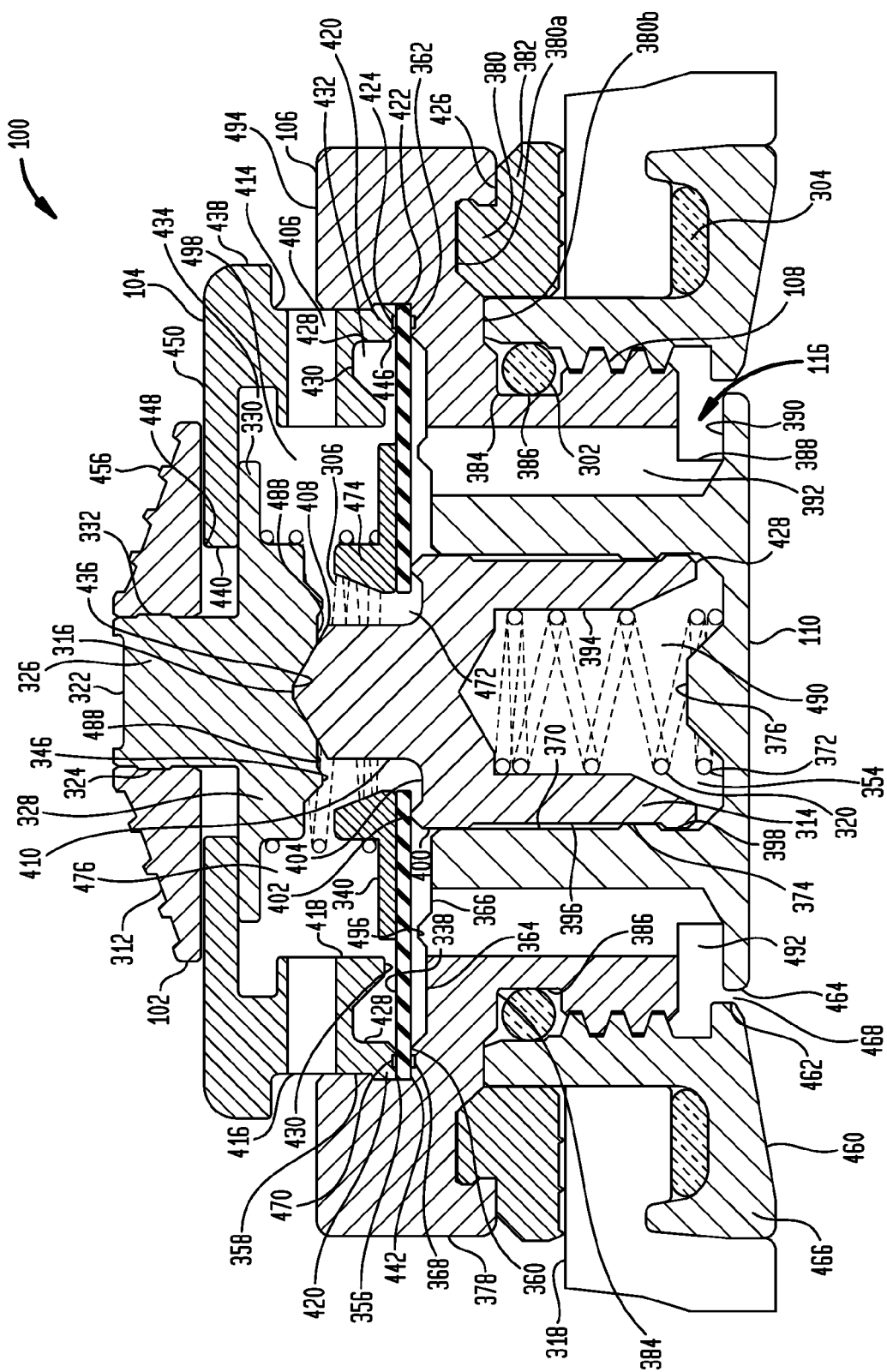
FIG. 3 is a cross-sectional view of the prosthetic valve depicted in FIGS. 1 and 2 taken along lines 3-3 of FIG. 4 and including a cross-sectional view of its associated housing and attachment to a prosthesis.

Turning now to FIGS. 2 and 3, body 106 is a tubular body machined to the free state shape illustrated in FIGS. 2 and 3. Body 106 has a large diameter open end with a substantially cylindrical inner wall 356. An internal bead or lip 358 projects inwardly (i.e., toward the axis of valve 100) from inner wall 356 under which a proximal edge of cap 104 may be fitted as discussed in greater detail below. The upper and lower portions of the inwardly facing surface of bead 358 are tapered axially outward at an angle of approximately 45 degrees. Such tapering facilitates the interlocking of cap 104 with body 106 as discussed in greater detail below. From bead 358, inner wall 356 of body 106 extends axially downward with a fixed radial diameter to corner 442. At corner 442, inner wall 356 transitions radially inward along substantially horizontal wall 360. Recess 362 is recessed in wall 360. The innermost end of wall 360 intersects the outermost end of recess 364, the latter of which slopes axially downward and radially inward at an angle of approximately 45 degrees. The innermost point of the floor of recess 364 intersects the base of protrusion 496, which is substantially frustoconical. The innermost point of protrusion 496 intersects the outermost portion of recess 366, which is recessed below the base of protrusion 496. The innermost point of recess 366 slopes axially downward and radially inward at an angle of approximately 45 degrees. Substantially rectangular recess 362 is provided for retaining diaphragm 338 as discussed in greater detail below. Substantially U-shaped recesses 364 and 366 are provided for the purpose of providing clearance for travel of diaphragm 338 and air flow. Recesses 364 and 366 also distribute air evenly across the downwardly facing surface of diaphragm 338. Protrusion 496 limits the downward motion of diaphragm 338 when operator 102 is indexed to vent mode. As discussed in greater detail below, during vent mode, diaphragm interface 402 is maintained at an elevation that is sufficiently lower than the upwardly facing end of protrusion 496 to create a path for bi-directional airflow that extends from the atmosphere located external to valve 100 through cap vent 406 into external vent 476 to recesses 364 and/or 366 to internal vent 392 to ring vent 468 and into the socket. At the innermost point of U-shaped recess 366, substantially cylindrical inner wall 370 begins. Inner wall 370 has a fixed radial diameter and an axial length that extends from the bottommost point of U-shaped recess 366 to floor 372 of body cavity 354. Inner wall 370 includes an internal bead or lip 374 under which a bottommost end of core 314 may be fitted as discussed in greater detail below. Floor 372 includes floor protrusion 376 over which core spring 320 may be positioned such that the axes of floor protrusion 376 and core spring 320 are substantially aligned. In the depicted embodiment of the present invention, floor protrusion has a frustoconical shape. This shape facilitates the holding of core spring 320 around floor protrusion 376 such that it is centered relative to body cavity 354 and core cavity 490 as discussed in greater detail below.

Figure 4:
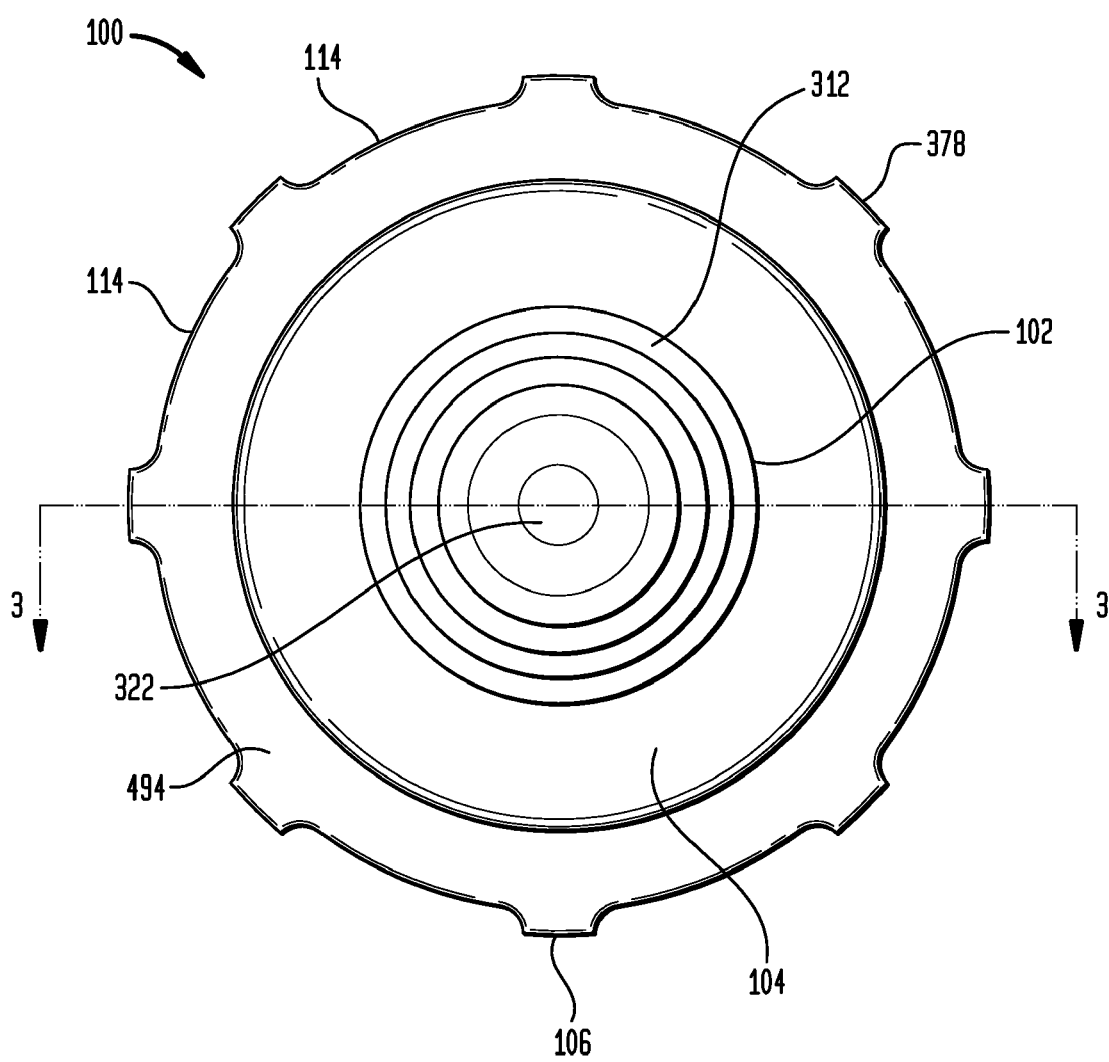
FIG. 4 is a top view of the prosthetic valve of FIG. 1 removed from its associated housing.

Body 106 has a large diameter open end with a substantially cylindrical exterior wall 378. The topmost end of exterior wall 378 transitions perpendicularly to upwardly facing wall 494, which is substantially horizontal. As best seen in the top view of FIG. 4, substantially cylindrical exterior wall 378 includes a plurality of substantially U-shaped grooves 114. Grooves 114 are recessed in exterior wall 378 and are located equidistantly around the perimeter of the upper portion of body 106. These grooves aid in the handling of valve 100 by breaking the otherwise smooth surface such that the valve may be more easily gripped without slippage. Although equidistantly spaced substantially U-shaped grooves are depicted in FIG. 4, other groove shapes and/or spacing may be substituted without departing from the scope of the present invention.

Referring back to FIG. 3, At the bottommost end of exterior wall 378, exterior wall 378 becomes wall 426, which extends radially inward in a substantially horizontal manner with the exception of recess 380. Recess 380 includes an outermost recess 380a and an innermost recess 380b. Outermost recess 380a includes a 45 degree bevel along its innermost axial surface and a U-shaped indentation along its outermost axial surface. This configuration of outermost recess 380a facilitates retention of washer 382, the latter of which is configured to mate to outermost recess 380a. However, alternate mating configurations of outermost recess 380a and washer 382 may be substituted without departing from the scope of the present invention. Washer 382 is ribbed on its downwardly facing surface to provide a tighter fit or clamp between washer 382 and prosthesis 318 when valve 100 is threaded into housing 460. Washer 382 also reduces the torque required to obtain maximum compression of housing seal O-ring 304 beneath prosthesis 318 when valve 100 is threaded into housing 460. Innermost recess 380b also includes a 45 degree bevel along its innermost axial surface and it does not have an outermost axial surface. Outermost recess 380b is configured to mate with and/or allow entry of a component threaded onto threads 108 (e.g., housing 460).

Once wall 426 extends to corner 384, it transitions perpendicularly to wall 386. Threads 108 protrude from wall 386. Below threads 108, exterior wall 386 converges axially downward and radially inward until it intersects perpendicularly with exterior axial surface 388 of connector section 116 (best seen in FIG. 1). Connector section 116 is tubular and exterior axial surface 388 has a fixed radial diameter. At its bottommost edge, exterior axial surface 388 intersects perpendicularly with wall portion 390. Wall portion 390 is the upwardly facing surface of a large diameter U-shaped bulge which forms the exterior surface of base 110. U-shaped bulge includes outwardly facing surface 464.

Body 106 includes a plurality of internal vents 392. In the depicted embodiment, internal vents 392 are substantially cylindrical and extend axially from the floor of U-shaped recesses 364 and 366 and the base of protrusion 496, as discussed in greater detail below, to a point below the bottommost thread 108 at which point such vents intersect groove 492, the latter of which extends outward in a radial direction and passes below the bottommost thread 108 through exterior axial surface 388 of connector section 116. Although two cylindrical internal vents 392 are depicted in FIG. 3, varying shapes and/or quantities may be substituted without departing from the scope of the present invention.

The interior of body 106 is designed to interlock with core 314. Core 314 is a partially tubular body machined to the free state shape illustrated in FIG. 3. The bottom portion of core 314 includes a substantially cylindrical core cavity 490 centered about the axis of core 314 and bounded by inner walls 394. As axial inner walls 394 extend downward, inner walls 394 taper radially outward and axially downward in a conical manner. The downwardly facing surface 428 of core 314 is substantially horizontal. Exterior walls 396 of the substantially cylindrical portion of core 314 include lower and upper beads or lips 398 and 400, respectively.

Lower bead 398 protrudes from exterior wall 396 to approximately the same extent that internal bead 374 protrudes from inner wall 370. The radial sides of lower bead 398 and internal bead 374 are tapered in an inverse frustoconical manner. Such shaping facilitates the interlocking of core 314 and body 106 in a manner that retains core 314 therein. That is, as core 314 is slid into substantially cylindrical body cavity 354, the conically tapered sides of bead 398 and internal bead 374 facilitate a radially inward motion of bead 398 as it butts up against internal bead 374 until core 314 is slid past internal bead 374 at which point core 314 elastically returns to its original shape. In this original shape, core 314 is retained within substantially cylindrical body cavity 354 due to the impediment of the axial motion of bead 398 by internal bead 374. This retention also acts to retain core spring 320 within substantially cylindrical core cavity 490 for the purposes described in greater detail below.

The topmost end of upper bead 400 intersects perpendicularly with an upwardly facing surface that converges radially inward and includes diaphragm interface 402 and recess 404.

Diaphragm interface 402 is substantially frustoconical. The substantially horizontal tip of diaphragm interface 402 contacts the downwardly facing surface of diaphragm 338. In addition to facilitating donning and doffing of a prosthesis as well as a comfortable and reliable fit, valve 100 is also set to a predetermined setpoint (e.g., 0.5 PSI) to allow the valve to completely displace any air that previously entered the prosthetic socket when a load is applied to the residual limb.

In accordance therewith, any air passing into the prosthetic socket also passes through ring vent 468 to groove 492 to internal vent 392 and through recesses 364 and 366 thereby applying pressure to the downwardly facing surface of diaphragm 338 such that it separates from diaphragm interface 402 against the pressure of diaphragm spring 306 to a sufficient extent to allow the valve to completely displace the air that previously entered the prosthetic socket. This displaced air passes from internal vent 392 to external vent 476 to cap vent 406 at which point it may pass to the environment located external to valve 100. Recess 404 ensures a clear path for the air relieved through the separation of the downwardly facing surface of diaphragm 338 and diaphragm interface 402.

The innermost point of recess 404 intersects with the bottommost point of exterior wall 410, the latter of which extends axially upward with a fixed radial diameter until corner 408. At corner 408, exterior wall 410 tapers radially inward and axially upward in a substantially frustoconical manner. Tip 436 includes a substantially flat upwardly facing surface, which is designed to interlock with portions of the downwardly facing surface of operator retainer 322 as discussed in greater detail below.

The interior of body 106 is also designed to interlock with cap 104. Cap 104 is a tubular body machined to the free state shape illustrated in FIGS. 1-4 with a centrally located aperture 498. The uppermost portion of core 314 passes at least partially into said bottommost portion of centrally located aperture 498, and the bottommost portion of operator retainer 322 passes at least partially into said topmost portion of centrally located aperture 498. Cap 104 has an outwardly facing surface 438 (i.e., the surface facing away from the axis of valve 100). The topmost and bottommost ends of outwardly facing surface 438 curve radially inward. The innermost portion of the bottommost end of outwardly facing surface 438 extends radially inward in a substantially horizontal manner until it extends to corner 414. Outwardly facing surface 438 transitions perpendicularly to wall 416, which has a substantially fixed radial diameter, extends axially downward, and through which outermost portions of a plurality of cap vents 406 pass. In the depicted embodiment, cap vents 406 are substantially cylindrical and extend radially inward through wall 416 and through inwardly facing wall 418. Cap vents 406 allow air to flow in and out of valve 100 as needed during donning and doffing of the prosthesis as well as during normal wear of the prosthesis (i.e., to facilitate complete displacement of any air that previously entered into the prosthetic socket when a load is applied to the residual limb). Although two cylindrical cap vents 406 are depicted in FIG. 3, varying shapes and/or quantities may be substituted without departing from the scope of the present invention.

An external lip or bead 420 protrudes from wall 416 to approximately the same extent that bead 358 protrudes from inner wall 356. The substantially rectangular shape of the recess created directly below bead 358 facilitates the interlocking of the rectangular bead 420 beneath bead 358 in a manner that attaches cap 104 to body 106. Also, the tapering of the upper and lower portions of the inwardly facing surface of bead 358 in an axially outward manner also facilitates snapping of cap 104 into body 106. That is, when the bottommost end of cap 104 is inserted into the large diameter open end of body 106, the approximately 45 degree tapering of the upper portion of the inwardly facing surface of bead 358 contacts the outwardly facing surface of bead 420 and causes it to gradually contract inward as downward pressure is exerted on cap 104. Once bead 420 is fully contracted, it remains in this state as further downward pressure is applied to cap 104 until the outwardly facing surface of bead 420 begins contact with the approximately 45 degree tapering of the lower portion of the inwardly facing surface of bead 358. With continued downward pressure exerted onto cap 104, bead 420 elastically returns to its original shape at a point at which bead 420 is located below bead 358 and the rectangular bead 420 has fully filled the substantially rectangular recess located below bead 358. In this original shape, cap 104 is retained below bead 358 due to the impediment of the upward axial motion of bead 420 by internal bead 358. In this manner, the other components of valve 100 (e.g., diaphragm 338, operator retainer 322, core 314, core spring 320, and diaphragm spring 306) are also coupled to body 106.

Diaphragm 338 is a disc-shaped diaphragm having a centrally located diaphragm aperture 472. The thickness of diaphragm 338 is slightly greater than the gap between the downwardly facing surface of cap 104 and wall 360 when cap 104 is inserted, or snapped into, body 106. The difference in these dimensions causes compression of diaphragm 338 near its perimeter. This compression causes radial portions of the substantially flat downwardly and upwardly facing surfaces of diaphragm 338 to fill recesses 362 and 424, respectively, thereby forming diaphragm protrusions 368 and 470.

Diaphragm 338 also includes diaphragm backer 340 which is substantially disc shaped and includes a centrally located aperture. The innermost portion of diaphragm backer 340 includes an upwardly facing protrusion 474 that is substantially tubular and extends across approximately one-third of the upwardly facing surface of diaphragm backer 340. The inwardly facing surface of protrusion 474 is tapered radially outward at an angle of approximately 30 degrees as it extends axially upward. The outwardly facing surface of protrusion 474 is cylindrical and it engages the bottommost inwardly facing surfaces of diaphragm spring 306. This engagement centers diaphragm spring 306 such that it is substantially axially aligned with valve 100 and the other central components thereof. The uppermost end of the outwardly facing surface of protrusion 474 is curved. The disc-shaped portion of diaphragm backer 340 extends radially outward across the inner one-half (approximately) of diaphragm 338 and is designed to evenly distribute the load imparted by diaphragm spring 306 across diaphragm 338 such that diaphragm 338 acts as a piston against diaphragm spring 306.

During assembly of valve 100, diaphragm 338 is placed atop body 106 such that core 314 passes through diaphragm aperture 472 and radial portions of the downwardly and upwardly facing surfaces of diaphragm 338 are compressed between the downwardly facing surface of cap 104 and the upwardly facing surface of wall 360, thereby forming protrusions 368 and 470, respectively, as discussed in greater detail above. The interlocking of diaphragm protrusions 368 and 470 with recesses 362 and 424 eliminates lateral slippage or other movement of diaphragm 338 and reduces distortion and preloading of diaphragm 338. Therefore, this feature improves the operational consistency of valve 100. Although diaphragm 338 is described with specificity, other diaphragms having varying shapes and/or retention methods may be substituted without departing from the scope of the present invention. Also, although the interlocking of cap 104 to body 106 depicted in FIGS. 1 through 4 has been described in great detail, other methods of interlocking cap 104 and body 106 may be substituted without departing from the scope of the present invention.

At its lowest point, wall 416 transitions perpendicularly to downwardly facing surface 422, which converges radially inward in a substantially horizontal manner. Located along surface 422 is rectangular recess 424 provided for retaining diaphragm 338 as discussed above. The innermost point of surface 422 extends radially inward and axially upward at an angle of approximately 45 degrees to corner 446. From corner 446, inwardly facing wall 428 extends axially upward at a fixed radial diameter until it perpendicularly intersects downwardly facing surface 430. Located along surface 430 is recess 432, whose inward wall extends axially downward and radially inward at an approximately 45 degree angle.

Cap 104 has a large diameter open end with a substantially cylindrical interior wall 418. Substantially cylindrical cap vents 406 pass through wall 418 as discussed above. The topmost end of wall 418 intersects with the innermost bottom edge of substantially rectangular recess 434. Recess 434 is provided to receive ledge 330 of operator retainer 322 during lateral movement thereof as discussed in greater detail below. From recess 434, interior wall 418 converges radially inward in a substantially horizontal manner. At the innermost point of wall 418, substantially cylindrical inwardly facing surface 440 begins. The topmost and bottommost ends of inwardly facing surface 440 are curved radially outward. At its topmost end, inwardly facing surface 440 transitions at corner 448 to upwardly facing surface 450, which extends radially outward in a substantially horizontal manner until it meets outwardly facing surface 438. The intersection of upwardly facing surface 450 and outwardly facing surface 438 is curved.

Still referring to FIG. 3, operator 102 is coupled to cap 104 via operator retainer 322. As depicted, operator retainer 322 is a partially cylindrical body machined to the free state shape illustrated in FIG. 3. Operator retainer 322 includes substantially cylindrical operator retainer head 326 and operator retainer base 328. The outwardly facing surface of operator retainer head 326 includes a bead or lip 324. Bead 324 has a frustoconical shape designed for interlocking with operator recess 332 which also has a frustoconical shape. This interlocking couples operator 102 to operator retainer 322 such that these two components move in unison when operator 102 is actuated by a user as discussed in further detail below.

Operator retainer base 328 includes ledge 330. Ledge 330 extends radially outward from the topmost end of operator retainer base 328 in the form of a disc. The upwardly facing surface of ledge 330 moves along the adjacent downwardly facing surface of cap 104 when a user actuates valve 100 from a first mode to a second mode as discussed in greater detail below. In addition, ledge 330 moves into cap recess 434 as needed during indexing of valve 100 from a first mode to a second mode as discussed in greater detail below.

Below ledge 330, operator retainer base 328 is substantially cylindrical. This shape accommodates the wrapping of the uppermost end of diaphragm spring 306 around the outwardly facing surface of the bottommost cylindrical portion of operator retainer base 328. The downwardly facing surface of operator retainer 322 includes a centrally located substantially frustoconical recess 316 as well as a peripherally located substantially frustoconical protrusion 346 between which is located substantially horizontal surface 488. Substantially frustoconical tip 436 interlocks with recess 316 or the inwardly facing surface of protrusion 346 and/or the surface 488 depending upon the position of operator 102 as indexed by a user.

Operator 102 has a frustoconical shape with an aperture passing through its center. The aperture is sized to snugly encircle substantially cylindrical operator retainer head 326. The inwardly facing walls of operator 102 include operator recesses 332 for interlocking with bead 324 of operator retainer 322 as discussed above.

During the "displacement mode" of operation of valve 100 (i.e., while valve 100 is set to displace any air that enters the prosthetic socket), operator retainer 322 remains substantially axially aligned with core 314 via the interlock of recess 316 and tip 436 and the pressure exerted upwardly upon core 314 by core spring 320 (i.e., operator retainer 322 is axially centered relative to valve 100 and the valve is indexed to "displacement mode"). That is, core spring 320 holds the upwardly facing surface of tip 436 adjacent the downwardly facing surface of recess 316. The substantially frustoconical shape of recess 316 limits the upward movement of substantially frustoconical tip 436 of core 314. Operator retainer 322 also acts to hold operator 102 in a centered position via the interlocking of operator bead 324 and operator retainer recess 332 as described in greater detail above.

The retention of core 314 in a position in which it is substantially axially aligned with body 106 maintains contact between diaphragm interface 402 and diaphragm 338 such that any air that previously entered the prosthetic socket may be displaced when a load is applied to the residual limb as discussed in greater detail above. Displacing the air that enters the prosthetic socket maintains the comfort and fit of the prosthesis.

Alternatively, when the user wishes to remove the prosthesis, the user actuates operator 102 substantially laterally to the "vent mode" to facilitate prosthesis donning and doffing. The present invention allows operator 102 to be moved substantially laterally in any direction (i.e., operator 102 may be actuated omni-directionally) desired by the user. As operator 102 is moved substantially laterally, the substantially frustoconical shape of recess 316 creates a downward force on tip 436 and core 314 which gradually contracts core spring 320 as the upwardly facing surface of tip 436 is moved downwardly along the inwardly facing wall of recess 316. During lateral movement of operator 102, the outwardly facing surface of operator retainer head 326 moves laterally in unison toward the corresponding portion of inwardly facing surface 440 of cap 104. Additionally, this lateral movement causes the curved outwardly facing surface of ledge 330 to move radially outward until it enters cap recess 434. Lateral movement of operator 102 continues until the outwardly facing surface of operator retainer head 326 abuts the corresponding portion of inwardly facing surface 440 of cap 104. At this point, tip 436 is in contact with the downwardly facing surface 488 and/or the inwardly facing surface of protrusion 346 and is held in touch therewith via core spring 320, which expands to hold the upwardly facing surface of tip 436 adjacent the downwardly facing surface 488 and/or the inwardly facing surface of protrusion 346 (i.e., the slide is indexed to an off-center position and to "vent mode"). The user will experience an auditory click when indexing valve 100 from its displacement mode to its vent mode due to the rapid unwinding of the lateral force that occurs when tip 436 slides rapidly across surface 488 to contact the inwardly facing surface of protrusion 346. Similarly, the user will also hear an auditory click when indexing valve 100 from its vent mode to its displacement mode due to the rapid drop of tip 436 into recess 316. That is, the auditory click indicates to the user that the slide has been properly actuated from one mode of operation to the other mode of operation.

The movement of tip 436 from recess 316 to the inwardly facing surface of protrusion 346 lowers the axial position of core 314 which causes a maintained separation of diaphragm interface 402 and diaphragm 338. This separation allows air to travel from the atmosphere located external to valve 100 through cap vent 406 into external vent 476 to recesses 364 and 366 to internal vent 392 to groove 492 to ring vent 468 and into the socket, thereby allowing the vacuum present in the socket to be relieved. This relief facilitates removal of the prosthesis from the user's residual limb. In contrast to other prosthetic valves known in the art which require a user to hold a button in a depressed position throughout removal of the prosthesis, once operator 102 of the present invention is actuated by the user, operator 102 remains in a vent position (i.e., the position in which tip 436 is adjacent the inwardly facing surface of protrusion 346 and air moves freely in and out of the socket) throughout prosthesis donning and doffing which frees both of the user's hand.

Similarly, a user may index the valve to vent position during donning of the prosthesis to substantially reduce the force required to don the prosthesis. This occurs due to the ability of valve 100 to allow the air to escape from the prosthetic socket. Once the user has finished donning the prosthesis, the user actuates operator 102 to the displacement operation position (i.e., the position in which tip 436 is located within recess 316 and the diaphragm displaces any air that previously entered into the prosthetic socket when a load is applied to the residual limb).

As best seen in the top view of FIG. 4, operator 102 includes a plurality of substantially circular grooves 312. As best seen in FIG. 3, grooves 312 are substantially inverse frustoconical and are recessed in angled upwardly facing wall 456. Grooves are also located equidistantly along the radial extent of upwardly facing wall 456. These grooves aid in the actuation of operator 102 by breaking the otherwise smooth surface such that operator 102 may be more easily actuated (in a substantially lateral manner) without slippage. Although four equi-distantly spaced substantially circular grooves are depicted in FIGS. 3 and 4, other groove quantities, shapes, and/or spacing may be substituted without departing from the scope of the present invention.

As depicted in FIG. 3, threads 108 facilitate coupling of valve 100 to a housing such as housing 460. That is, valve 100 is coupled to housing 460 via threading of threads 108 of valve 100 into the substantially cylindrical, inversely threaded cavity of housing 460. Inwardly facing surface 462 of the body 466 of housing 460 cooperates with outwardly facing surface 464 of base 110 to form ring vent 468. Ring vent 468 is a substantially circular vent that encircles base 110 and is in communication with groove 492 and internal vent 392. Ring vent 468, groove 492, and internal vent 392 allow air to flow from the socket cavity to recesses 364 and 366, external vent 476, and cap vent 406 under the control of diaphragm 338 as discussed in greater detail above. Furthermore, in the embodiments of the present invention depicted in FIGS. 1-4, housing 460 includes housing O-ring 304. Housing 460 provides support to the interior of prosthesis 318 and O-ring 304 forms a seal between housing 460 and prosthesis 318. Additionally, housing 460 includes body O-ring 302 which forms a seal between housing 460 and body 106.

In the embodiment of the present invention depicted in FIGS. 1-4, the following materials are used: 1) operator 102, cap 104, operator retainer 322, body 106, core 314, washer 380, and housing 460 are made of Delrin® acetal resin; 2) springs 320 and 452 are made of stainless steel; 3) diaphragm backer 340 is made of polyvinyl chloride ("PVC"); and 4) diaphragm 338 and O-rings 302 and 304 are made of Buna N. However, any other suitable material(s) may be substituted for any of the aforementioned materials without departing from the scope of the present invention.

Referring lastly to FIG. 5, depicted is a flowchart of the steps of a method for using a valve such as valve 100 in accordance with one embodiment of the present invention. Process 500 starts at 502, at which a valve in accordance with the present invention is installed in a socket port. For example, in the embodiment of the present invention depicted in FIGS. 1-4, housing 460 is passed from the interior of the prosthetic socket through a molded aperture in the prosthesis. Valve 100 is then threaded into housing 460 from the opposite side of the prosthesis such that valve 100 and housing 460 clamp the prosthesis between washer 380 and housing O-ring 304 as depicted in FIG. 3.

Process 500 then proceeds to 504 at which the valve slide is laterally actuated to a "vent mode" of operation. This mode of operation indexes the diaphragm interface to a position in which it is not in contact with the diaphragm and the socket is connected to the atmosphere external to the valve. This position allows free flow of air from the interior of the prosthetic valve to its exterior in order to avoid back pressure during donning of the prosthesis. This position allows the prosthesis to be mounted to the residual limb via creation of a seal between the residual limb and the interior wall of the prosthetic socket during prosthesis attachment.

Next, at 506, the prosthesis is donned. Process 500 then proceeds to 507 at which the valve slide is laterally actuated to a "displacement mode" of operation. The displacement mode of operation indexes the diaphragm interface to a position in which it is in contact with the diaphragm. This position is maintained unless air enters the socket. If air enters the socket, the diaphragm operates to completely displace the air such that a reliable and comfortable fit is maintained.

Process 500 then proceeds to 508 at which a user wears the prosthesis. In the displacement mode of operation, the diaphragm completely displaces any air that previously entered into the prosthetic socket when a load is applied to the residual limb during normal wear of the prosthesis.

When a user wishes to remove a prosthesis, process 500 proceeds to 510 at which the valve slide is laterally actuated to the "vent mode" of operation. This mode of operation indexes the diaphragm interface to a position in which it is not in contact with the diaphragm and the socket is connected to the atmosphere external to the valve. This position removes the vacuum, or near vacuum, within the socket such that the prosthesis may be more easily removed. Finally, process 500 proceeds to 512 at which the prosthesis is removed.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. An apparatus for facilitating prosthesis donning and doffing comprising:
   a body including a body cavity, at least one internal vent, and at least one external vent;
   a core, said core including a core tip, a core cavity, and a diaphragm interface, said core located at least partially within said body cavity;
   a core spring located at least partially internal to said core cavity, a first end of said core spring in contact with a surface of said core cavity, a second end of said core spring in contact with a surface of said body cavity;

an operator, said operator including an operator aperture;

an operator retainer, said operator retainer including a base and a head, an external surface of said head coupled to an interior surface of said operator aperture, said base including a recess and an operator retainer protrusion, said operator retainer protrusion located external to the periphery of said recess, an uppermost point of said recess in contact with said core tip when said operator is axially centered relative to said apparatus, an inwardly facing surface of said operator retainer protrusion in contact with said core tip when said operator is indexed to an off-center position, said operator maintained in an axially centered position due to said contact of said recess with said core tip, said operator maintained in an off-center position due to said contact of said inwardly facing surface of said operator retainer protrusion with said core tip; and a diaphragm, said diaphragm including a diaphragm aperture, said core passing through said diaphragm aperture, said diaphragm in contact with said diaphragm interface when said operator is axially centered relative to said apparatus, said diaphragm separated from said diaphragm interface when said operator is indexed to an off-center position.

2. An apparatus according to claim 1 further comprising:
a cap, said cap including a cap aperture, said core passing at least partially into said cap aperture, said operator retainer passing at least partially into said cap aperture, said cap including at least one cap vent.

3. An apparatus according to claim 2, wherein said at least one cap vent passes radially throughout a wall of said cap.

4. An apparatus according to claim 2, said cap further comprising:
a cap bead, said cap bead having an external surface having a nearly identical shape as an internal surface of a body recess located in said body for interlocking said cap bead with said body recess.

5. An apparatus according to claim 1 wherein said diaphragm includes a diaphragm backer.

6. An apparatus according to claim 2, said operator retainer further comprising:
an operator retainer ledge, said operator retainer ledge located external to a cap recess when said operator is axially centered relative to said apparatus, said operator retainer ledge located internal to said cap recess when said operator is indexed to an off-center position.

7. An apparatus according to claim 1 wherein said operator includes at least one groove.

8. An apparatus according to claim 1 wherein an outwardly facing surface of said body includes at least one groove.

9. An apparatus according to claim 1 wherein said recess and said core tip are substantially frustoconically shaped.

10. An apparatus according to claim 1 further comprising:
a tubular housing having housing threads along at least a portion of inwardly facing surface of said housing for threading said housing to body threads located on at least a portion of an outwardly facing surface of said body.

11. An apparatus according to claim 1 wherein an auditory click is generated upon sliding of said operator from said axially centered position to said off-center position.

12. An apparatus according to claim 5 further comprising:
a diaphragm spring, a first end of said diaphragm spring encircling an outwardly facing surface of a bottommost portion of said operator retainer base, a second end of said diaphragm spring encircling an outwardly facing surface of said diaphragm backer.

13. An apparatus for facilitating prosthesis donning and doffing comprising:
a body including a centrally located body cavity, at least one internal vent, at least one external vent, a diaphragm bead body recess, and a cap body recess;

a core, said core including a core tip, a core cavity, and a diaphragm interface, said core located at least partially within said body cavity;

a core spring located at least partially internal to said core cavity, a first end of said core spring in contact with a surface of said core cavity, a second end of said core spring in contact with a surface of said body cavity;

an operator, said operator including an operator aperture;

an operator retainer, said operator retainer including a base and a head, an external surface of said head coupled to an interior surface of said operator aperture, said base including an operator retainer recess, and an operator retainer protrusion, said operator retainer protrusion located external to the periphery of said operator retainer recess, an uppermost point of said operator retainer recess in contact with said core tip when said operator is axially centered relative to said apparatus, an inwardly facing surface of said operator retainer protrusion in contact with said core tip when said operator is indexed to an off-center position, said operator maintained in an axially centered position due to said contact of said operator retainer recess with said core tip, said operator maintained in an off-center position due to said contact of said inwardly facing surface of said operator retainer protrusion with said core tip, said operator retainer including an operator retainer ledge, said operator retainer ledge located external to a cap recess when said operator is axially centered relative to said apparatus, said operator retainer ledge located internal to said cap recess when said operator is indexed to an off-center position;

a diaphragm, said diaphragm including a diaphragm aperture, said core passing through said diaphragm aperture, said diaphragm in contact with said diaphragm interface when said operator is axially centered relative to said apparatus, said diaphragm separated from said diaphragm interface when said operator is indexed to an off-center position;

a diaphragm backer, said diaphragm backer shaped as a disc having a diaphragm backer protrusion located on an upwardly facing surface of said disc;

a diaphragm spring, a first end of said diaphragm spring encircling an outwardly facing surface of a bottommost portion of said operator retainer base, a second end of said diaphragm spring encircling an outwardly facing surface of said diaphragm backer protrusion; and a cap, said cap including a cap aperture, a cap recess, at least one cap vent, and a cap bead, said core passing at least partially into said cap aperture, said operator retainer passing at least partially into said cap aperture, said cap bead having a first external surface with a nearly identical shape as a first internal surface of said cap body recess for interlocking said cap with said body, said cap vent passing radially through a wall of said cap.

14. An apparatus according to claim 12 wherein said operator includes at least one groove.

15. An apparatus according to claim 12 wherein an outwardly facing surface of said body includes at least one groove.

16. An apparatus according to claim 12 wherein an auditory click is generated upon sliding of said operator from said axially centered position to said off-center position.

* * * * *